United States Patent [19]
Hillman et al.

[11] Patent Number: 5,882,890
[45] Date of Patent: Mar. 16, 1999

[54] NUCLEIC ACIDS ENCODING NOVEL REGULATORS OF G-PROTEIN SIGNALING

[75] Inventors: Jennifer L. Hillman, Mountain View; Surya K. Goli, Sunnyvale, both of Calif.

[73] Assignee: Incyte Pharmaceuticals, Inc., Palo Alto, Calif.

[21] Appl. No.: 829,110

[22] Filed: Mar. 31, 1997

[51] Int. Cl.$^6$ .................................................. C12N 15/12
[52] U.S. Cl. ................ 435/691; 435/252.3; 435/254.11; 435/320.1; 435/325; 536/23.5; 536/24.31
[58] Field of Search .................................. 435/69.1, 325, 435/320.1, 252.3, 254.11; 536/23.5, 24.3, 24.31

[56] References Cited

PUBLICATIONS

Hillier, L. et al., "The WashU–Merck EST Project", Emest4 Database Entry Hs046238, Accession No. H70046, (25 Oct. 1995), XP002069928.

Druey, K.M. et al., "Inhibition of G–protein–mediated MAP kinase activation by a new mammalian gene family", *Nature*, 379: 742–746 (1996).

Hong, J.X. et al., J.X. et al., "Isolation and Characterization of a Novel B Cell Activation Gene", *J. Immunol.*, 150: 3895–3904 (1993) (GI 299705).

Siderovski, D.P. et al., "A Human Gene Encoding a Putative Basic Helix–Loop–Helix Phosphoprotein Whose mRNA Increases Rapidly in Cycloheximide–Treated Blood Mononuclear Cells", *DNA Cell Biol.*, 13: 125–147 (1994).

Druey, K., (Direct Submission), GenBank Sequence Database (Accession U27768), National Center for Biotechnology Information, National Library of Medicine, Bethesda, Maryland, 20894 (GI 1216373).

*Primary Examiner*—Sally P. Teng
*Attorney, Agent, or Firm*—Leanne C. Price, Esq.; Lucy J. Billings, Esq.; Incyte Pharmaceuticals, Inc.

[57] ABSTRACT

The present invention provides two regulators of G-protein signaling (designated individually as RGPS-1 and RGPS-2, and collectively as RGPS) and polynucleotides which identify and encode RGPS. The invention also provides expression vectors, host cells, agonists, antibodies and antagonists. In addition, the invention also provides methods for producing RGPS and for treating or preventing disorders associated with expression of RGPS.

8 Claims, 11 Drawing Sheets

```
                   9             18             27             36             45             54
5' NCG CCT ATA    ATG AGA CAG    TAA AAT TCT    TTT ACT CTG    GGA AAA ATA    AAA TGC TGG 63             72             81             90             99            108
GTG TCT CAC    AAA ATT TCA    GAA CCT GAT    TTC AAA CGG    ATC ATA ACA    AAG AGG AGA 117            126            135            144            153            162
TCA AAT TTA    GCA TGG ACT    GCT CGA CAG    GAT ACA TTT    GTC AAT GGA    ATG TTT 171            180            189            198            207            216
CCA CAT ATT    ATA CCA ACA    TGA GAA AAA    AAT GAT CAT    TGT TTA TTT    GAA GCT 225            234            243            252            261            270
TGA AAA ATG    AGC AGG AAT    TGT TGG ATT    TGT AAA ATG    TGC AGA AAT    AAA TCT
        M       S   R   R      N   C   W      I   C   K      M   C   R      N   K   S 279            288            297            306            315            324
AAG AGG CCC    CCT TCA AAC    CTT ACC TTG    GAG GAA GTA    TTA CGG TGG    GCC CAG TCT
 K   R   P      P   S   N      L   T   L      E   E   V      L   R   W      A   Q   S 333            342            351            360            369            378
TTT GAA AAT    TTA ATG GCT    ACA AAA TAT    GGT CCA ATT    ATC TAT GCC    GCA TAT TTA
 F   E   N      L   M   A      T   K   Y      G   P   I      I   Y   A      A   Y   L
```

FIGURE 1A

```
        387         396         405         414         423         432
AAA ACG GAA CAC AGT GAC CAA AAT ATT CAA TTC TGG ATG GCA TGT GAA ACC TAT
 K   T   E   H   S   D   Q   N   I   Q   F   W   M   A   C   E   T   Y 441         450         459         468         477         486
AAG AAA ATT GCC TCA CGG TGG AGC AGA ATT TCT AGG GCA AAG CTT TAT AAG
 K   K   I   A   S   R   W   S   R   I   S   R   A   K   L   Y   K 495         504         513         522         531         540
ATT TAC ATC CAG CCA TCC CCT AGA GAG ATT AAC ATT GAC TGT AGT TCG ACA AGA
 I   Y   I   Q   P   S   P   R   E   I   N   I   D   C   S   S   T   R 549         558         567         576         585         594
GAG ACT ATC ATC AGG AAC ATT CAG GAA CCC ACT GAA ACA TGT TTT GAA GAA GCT
 E   T   I   I   R   N   I   Q   E   P   T   E   T   C   F   E   E   A 603         612         621         630         639         648
CAG AAA ATA GTC TAT ATG CAT ATG GAA AGG GAT TCC TAC CCC AGA TTT CTA AAG
 Q   K   I   V   Y   M   H   M   E   R   D   S   Y   P   R   F   L   K 657         666         675         684         693         702
TCA GAA ATG TAC CAA AAA CTT TTG AAA ACT ATG CAG TCC AAC AGT TTC TGA
 S   E   M   Y   Q   K   L   L   K   T   M   Q   S   N   S   F   *

711         720         729         738         747         756
CTA CAA CTC AAA AGT TTA AAT AGA AAA CAG TAT ATT GAA AGT GGT GGG TTT GAT
```

FIGURE 1B

```
          765        774        783        792        801        810
CTT TTT ATT TAG AAA CCC ACA AAA TCA GAA ACA CAG TAC AAA TAA AAC AGA AAT 819        828        837        846        855        864
CAA ACT ATA AGT TGA CTT TTA GTT CCT AAA AAG AAA CAT ATT TCA AAA GCA ATG 873        882        891        900        909        918
GAA TCT AGA ATT CTT ATA ACA TGA ATA ACA AAA TGT ACA GCA AGC CTA TGT AGT 927        936        945        954        963        972
TCA ATT AAT ATA TAA GGA CAA AGG TCT TCT TCA TGA TAC AAG CAT TAT AAA

981
GTT TTT ACT G 3'
```

FIGURE 1C

```
                    9          18          27          36          45          54
5' NCG GAC GGT GGG ACG GTT CCC GCG GGT CTG TCT CTT GCT TCG ACA GTG TTT GGA 63          72          81          90          99         108
   CGG AAC AGA TCC GGG GAC TCT CTT CCA GCC TCC GAC CGC CCT CCG ATT TCC TCT 117         126         135         144         153         162
   CCG CTT GCA ACC TCC GGG ACC ATC TTC TCG GCC ATC TCC TGC TTC TGG GAC CTG 171         180         189         198         207         216
   CCA GCA CCG TTT TTG TGG TTA GCT CCT TCT TGC CAA CCA ACC ATG AGC TCC CAG
                                                           M   S   S   Q 225         234         243         252         261         270
   ATT CGT CAG AAT TAT TCC ACC GAC GTG GAG GCA GCC GTC AAC AGC CTG GTC AAT
    I   R   Q   N   Y   S   T   D   V   E   A   A   V   N   S   L   V   N 279         288         297         306         315         324
   TTG TAC CTG CAG GCC TCC TAC ACC CTC TCT GGC TTC TAT TTC GAC CGC
    L   Y   L   Q   A   S   Y   T   L   S   G   F   Y   F   D   R 333         342         351         360         369         378
   GAT GAT GTG GCT CTG GAA GGC GTG AGC CAC TTC TTC CGC GAA CTG GCC GAG GAA
    D   D   V   A   L   E   G   V   S   H   F   F   R   E   L   A   E   E
```

FIGURE 2A

```
         387      396      405      414      423      432
GAA GCG CAA GGG CTA CGA GCG TCT GAA GAT GCA AAA CCA GCG TGG CGG CCG
 E   A   Q   G   L   R   A   S   P   E   D   A   K   P   A   W   R   P 441      450      459      468      477      486
CCG TCA GAC ATC CAC GAC AGC GAT GGC AGT TCC AGC AGC CAC CAG AGC CTC
 P   S   D   I   H   D   S   D   G   S   S   S   S   H   Q   S   L 495      504      513      522      531      540
AAG AGC ACA GCC AAA TGG GCG GCA TCC CTG GAG AAT CTG CTG GAA GAC CCA GAA
 K   S   T   A   K   W   A   A   S   L   E   N   L   L   E   D   P   E 549      558      567      576      585      594
GGC GTG AAA AGA TTT AGG GAA TTT TTA AAA AAG GAA TTC AGT GAA GAA AAT GTT
 G   V   K   R   F   R   E   F   L   K   K   E   F   S   E   E   N   V 603      612      621      630      639      648
TTG TTT TGG CTA GCA TGT GAA GAT TTT AAG AAA ATG CAA GAT AAG ACG CAG ATG
 L   F   W   L   A   C   E   D   F   K   K   M   Q   D   K   T   Q   M 657      666      675      684      693      702
CAG GAA AAG GCA AAG GAG ATC TAC ATG ACC TTT CTG TCC AGC AAG GCC TCA TCA
 Q   E   K   A   K   E   I   Y   M   T   F   L   S   S   K   A   S   S
```

FIGURE 2B

```
       711            720            729            738            747            756
CAG GTC AAC GTG GAG GGG CAG TCT CGG CTC AAC GAG AAG ATC CTG GAA GAA CCG
 Q   V   N   V   E   G   Q   S   R   L   N   E   K   I   L   E   E   P 765            774            783            792            801            810
CAC CCT CTG ATG TTC CAG AAA CTC CAG GAC CAG ATC TTT AAT CTC ATG AAG TAC
 H   P   L   M   F   Q   K   L   Q   D   Q   I   F   N   L   M   K   Y 819            828            837            846            855            864
GAC AGC TAC AGC CGC TTC TTA AAG TCT GAC TTG TTT TTA AAA CAC AAG CGA ACC
 D   S   Y   S   R   F   L   K   S   D   L   F   L   K   H   K   R   T 873            882            891            900            909            918
GAG GAA GAA GAA GAT TTG CCT GAT GCT CAA ACT GCA GCT CTC ATG AGA GCT TCC
 E   E   E   E   D   L   P   D   A   Q   T   A   A   L   M   R   A   S 927            936            945            954            963            972
AGA ATT TAT AAC ACA TGA GCC CCC AAA AAG CCG GGA CTG GCA GCT TTA AGA AGC
 R   I   Y   N   T 981            990            999           1008           1017           1026
AAA GGA ATT TCC TCT CAG GAC CGT CAA TGG GCC GGG TTT ATC ATT GCT TTG TTA TTT GTA 1035           1044           1053           1062           1071           1080
AGG ACT GAA ATG TAC AAA ACC CTT CAA TGG GAT GTG TGT TTT ATT AAC TGC TTC
```

FIGURE 2C

```
      1089           1098           1107      1116           1125      1134
ACC AGT AAA TTT TGC ATG ATG GCT AAG CTA ACA TAM MAA AAG AMT AAT AAT AAC 1143           1152           1161      1170           1179      1188
TTG GAA GTT TTA GTT TAC AAA ACA GAG ATT CCT TCA ACA CTG GNC ACG TCG AGC 1197           1206           1215      1224
ATT TTT NGT AGC TTN AAT TAA ACC TCA TGT AAT GCC CA 3'
```

```
 92  QPQSPREINIDSSTRETIIRNIQEPTETCFEEAQKIVYMH  158909
161  SSKASSQVNVEGQSRLNE-KILEEPHPLMFQKLQDIFNL   343504
129  HSDAAKQINIDFRTRESTAKKIKAPTPTCFDEAQKVIYTL  GI 299705
120  SVQATKEVNLDSCTREETSRNMLEPTITCFDEAQKKIFNL  GI 1216373

132  MERDSYPRFLKSEMYQKLLKTMQSN--------------  158909
200  MKYDSYSRFLKSDLFLKH-KRTEEEEDLPDAQTAAKRAS   343504
169  MEKDSYPRFLKSDIYLNLLNDLQANSLK-----------  GI 299705
160  MEKDSYRRFLKSRFYLDLVNPSSCGAEKQKGAKSSADCAS  GI 1216373

157  ---NSF                                    158909
239  RIYNT                                     343504
196                                            GI 299705
200  LVPQCA                                    GI 1216373
```

FIGURE 3B

NUCLEIC ACIDS ENCODING NOVEL REGULATORS OF G-PROTEIN SIGNALING

FIELD OF THE INVENTION

This invention relates to nucleic acid and amino acid sequences of novel regulators of G-protein signaling and to the use of these sequences in the diagnosis, prevention, and treatment of disorders associated with cell proliferation and inflammation.

BACKGROUND OF THE INVENTION

Signal transduction is the general process by which cells respond to extracellular signals. Extracellular signals are mediated through a cascade of biochemical reactions that begins with the binding of a signal molecule, e.g., a hormone, neurotransmitter, or growth factor, to a cell membrane receptor, and ends with the activation of an intracellular target molecule. This process of signal transduction regulates all types of cell functions including cell proliferation, differentiation, and gene transcription.

G-protein signaling is one of the important pathways of signal transduction. Specifically, receptors on a cell surface are coupled to a G-protein on the plasma membrane of the cell. The G-protein becomes activated when the receptor binds a messenger molecule, GTP. Activation of the G-protein leads to the production of the second messenger molecule, cAMP, which controls phosphorylation and activation of other intracellular proteins. The G-protein is deactivated by hydrolysis of the GTP by GTPase.

A second regulatory mechanism of G-protein signaling pathway involves a family of mammalian gene products termed regulators of G-protein signaling (RGS; Druey, K. M. et al. (1996) Nature 379: 742–746). These proteins negatively regulate the G-protein pathway by an unknown mechanism. Some 15 members of the RGS family have been identified. RGS family members are related structurally through similarities in an approximately 120 amino acid region termed the RGS domain and functionally by their ability to inhibit the interleukin (cytokine) induction of MAP kinase in cultured mammalian 293T cells (Druey et al., supra).

The first RGS family member BL34(RGS1) was found in activated B-lymphocytes associated with chronic lymphocytic leukemia (Hong, J. X. et al. (1993) J. Immunol. 150:3895–3904). RGS1 inhibits the activation of MAP kinase, a G-protein mediated event, which is induced by the binding of platelet-activating factor to a B-cell receptor. RGS2 (GOS8) was likewise found in lectin-stimulated peripheral blood mononuclear cells. Sequence similarities were noted between RSG2 and various genes involved in immune regulation of retroviruses and suppression of oncogenes (Siderovski D. P. et al. (1994) DNA Cell Biol. 13(2): 125–147).

RGS proteins regulate the G-protein signaling pathways directly by their ability to bind and inhibit G-protein function. Therefore, the discovery of new RGS proteins and the polynucleotides which encode them satisfies a need in the art by providing new diagnostic or therapeutic compositions useful in diagnosing, preventing, and treating disorders associated with cell proliferation and inflammation.

SUMMARY OF THE INVENTION

The present invention features two regulators of G-protein signaling, designated individually as RGPS-1 and RGPS-2, and collectively as RGPS, and characterized as having similarity to the regulators of G-protein signaling such as BL34 and RGS4.

Accordingly, the invention features substantially purified RGPS proteins RGPS-1 and RGPS-2 having the amino acid sequences shown in SEQ ID NO:1 and SEQ ID NO:3, respectively.

One aspect of the invention features isolated and substantially purified polynucleotides that encode RGPS proteins—RGPS-1 and RGPS-2. In a particular aspect, the polynucleotides are the nucleotide sequences of SEQ ID NO:2 and SEQ ID NO:4, respectively.

The invention also features a polynucleotide sequence comprising the complement of SEQ ID NO:2 and SEQ ID NO:4, or variants thereof. In addition, the invention features polynucleotide sequences which hybridize under stringent conditions to SEQ ID NO:2 and SEQ ID NO:4.

The invention additionally features nucleic acid sequences encoding polypeptides, oligonucleotides, peptide nucleic acids (PNA), fragments, portions or antisense molecules thereof, and expression vectors and host cells comprising polynucleotides that encode RGPS. The present invention also features antibodies which bind specifically to RGPS, and pharmaceutical compositions comprising substantially purified RGPS. The invention also features methods for stimulating cell proliferation using an RGPS or an agonist of RGPS and for treating or preventing disorders associated with cell proliferation and inflammation using an antagonist of RGPS.

BRIEF DESCRIPTION OF THE FIGURES

FIGS. 1A, 1B, and 1C show the amino acid sequence (SEQ ID NO:1) and nucleic acid sequence (SEQ ID NO:2) of RGPS-1. The alignment was produced using MacDNASIS PRO software (Hitachi Software Engineering Co., Ltd., San Bruno, Calif.).

FIGS. 2A, 2B, 2C, and 2D show the amino acid sequence (SEQ ID NO:3) and nucleic acid sequence (SEQ ID NO:4) of RGPS-2.

Figure 3A:
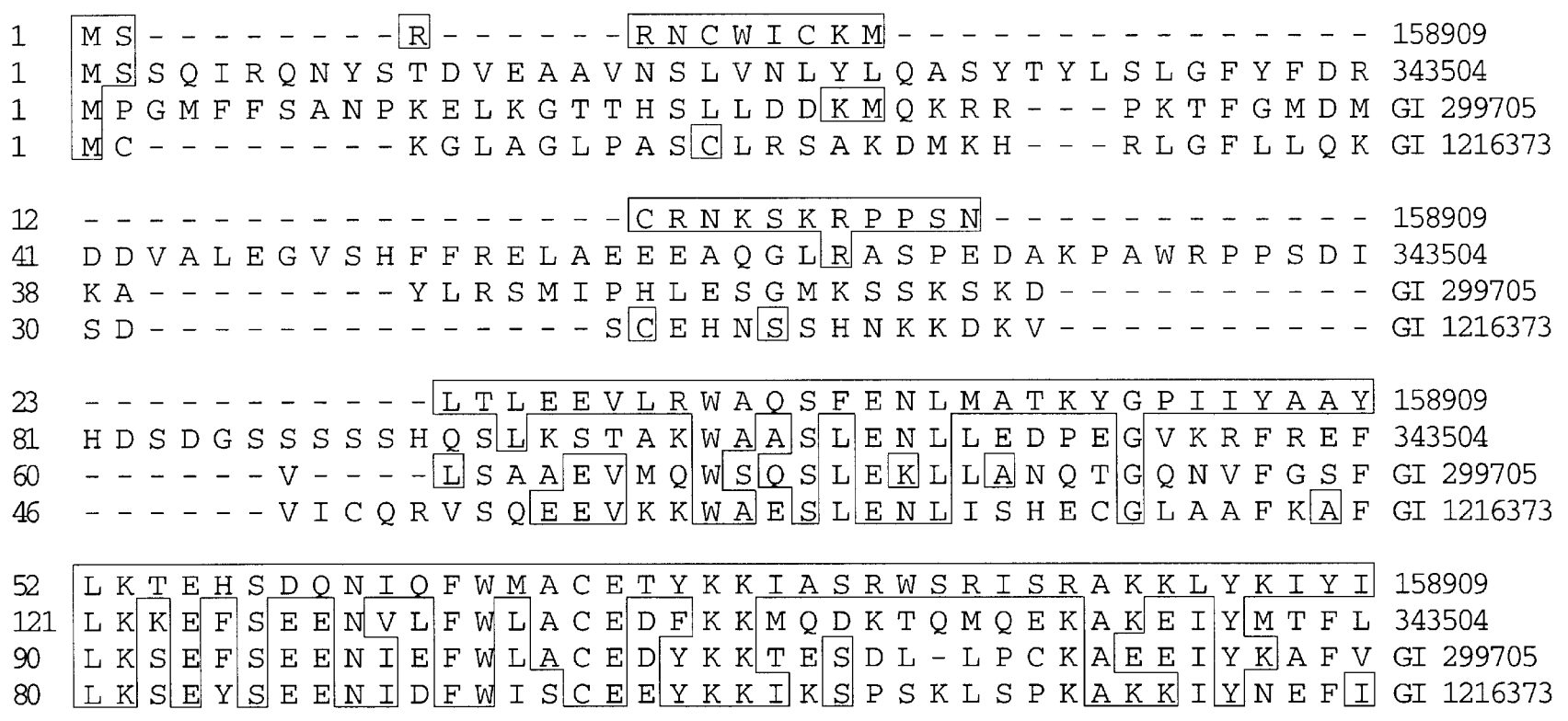

FIGS. 3A and 3B show the amino acid sequence alignments among RGPS-1 (SEQ ID NO:1), RGPS-2 (SEQ ID NO:3), human BL34 (GI 299705; SEQ ID NO:5), and human RGP4 (GI 1216373; SEQ ID NO:6). The alignment was produced using the multisequence alignment program of DNASTAR software (DNASTAR Inc, Madison Wis.).

DESCRIPTION OF THE INVENTION

Figure 4A:
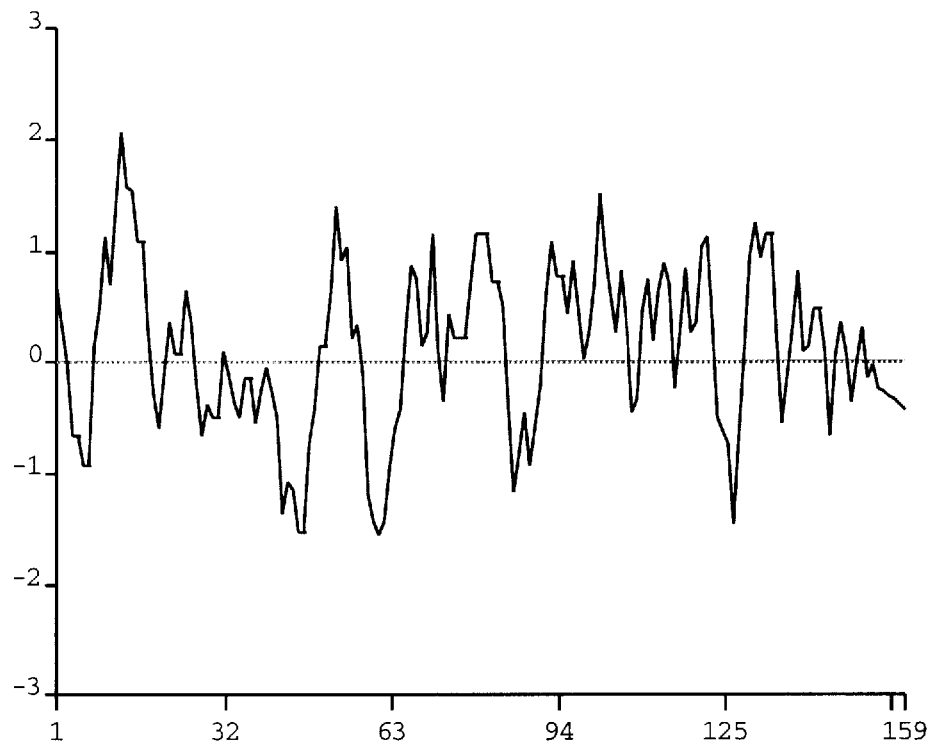
FIGS. 4A, 4B, 4C, and 4D show the hydrophobicity plots (MACDNASIS PRO software) for RGPS-1 (SEQ ID NO:1), RGPS-2, human BL34, and human RGP4, respectively. The positive X axis reflects amino acid position, and the negative Y axis reflects hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

RGPS, as used herein, refers to the amino acid sequences of substantially purified RGPS obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of RGPS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic RGPS, or any oligopeptide thereof, to induce a specific immune response in appropriate animals or cells and to bind with specific antibodies.

The term "agonist", as used herein, refers to a molecule which, when bound to RGPS, causes a change in RGPS which modulates the activity of RGPS. Agonists may include proteins, nucleic acids, carbohydrates, or any other molecules which bind to RGPS.

The terms "antagonist" or "inhibitor", as used herein, refer to a molecule which, when bound to RGPS, blocks or modulates the biological or immunological activity of RGPS. Antagonists and inhibitors may include proteins, nucleic acids, carbohydrates, or any other molecules which bind to RGPS.

The term "modulate", as used herein, refers to a change or an alteration in the biological activity of RGPS. Modulation may be an increase or a decrease in protein activity, a change in binding characteristics, or any other change in the biological, functional or immunological properties of RGPS.

The term "mimetic", as used herein, refers to a molecule, the structure of which is developed from knowledge of the structure of RGPS or portions thereof and, as such, is able to effect some or all of the actions of molecules related to regulators of G-protein signaling.

The term "derivative", as used herein, refers to the chemical modification of a nucleic acid encoding RGPS or the encoded RGPS. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human RGPS-1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding RGPS or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding RGPS in a sample and thereby correlates with expression of the transcript from the polynucleotide encoding the protein.

"Alterations" in the polynucleotide of SEQ ID NO:2 or SEQ ID NO:4, as used herein, comprise any alteration in the sequence of polynucleotides encoding RGPS including deletions, insertions, and point mutations that may be detected using hybridization assays. Included within this definition is the detection of alterations to the genomic DNA sequence which encodes RGPS (e.g., by alterations in the pattern of restriction fragment length polymorphisms capable of hybridizing to SEQ ID NO:2 or, SEQ ID NO:4), the inability of a selected fragment of SEQ ID NO:2 or SEQ ID NO:4 to hybridize to a sample of genomic DNA (e.g., using allele-specific oligonucleotide probes), and improper or unexpected hybridization, such as hybridization to a locus other than the normal chromosomal locus for the polynucleotide sequence encoding RGPS (e.g., using fluorescent in situ hybridization (FISH) to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind RGPS polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of regulators of G-protein signaling (RGPS-1 and RGPS-2, collectively referred to as RGPS), the polynucleotides encoding RGPS, and the use of these compositions for the diagnosis, prevention, or treatment of disorders associated with cell proliferation and inflammation.

Nucleic acid sequence encoding the human RGPS-1 of the present invention was first identified in Incyte Clone 158909 from an adenoid tissue cDNA library (ADENINB01) through a computer-generated search for amino acid sequence alignments. A consensus sequence, SEQ ID NO:2, was derived from the following overlapping and/or extended nucleic acid sequences (cDNA library from which derived): Incyte Clones 158909 and 160422 (ADENINB01).

Nucleic acid sequence encoding the human RGPS-2 of the present invention were first identified in Incyte Clone 343504 from a thymus tissue cDNA library (THYMNOT02) through a computer-generated search for amino acid sequence alignments. A consensus sequence, SEQ ID NO:4, was derived from the following overlapping and/or extended nucleic acid sequences (cDNA library from which derived): Incyte Clones 343504 (THYMNOT02), 841648 (PROSTUT05), 392629 (TMLR2DT01), and 003895 (HMC1NOT01).

Figure 4B:
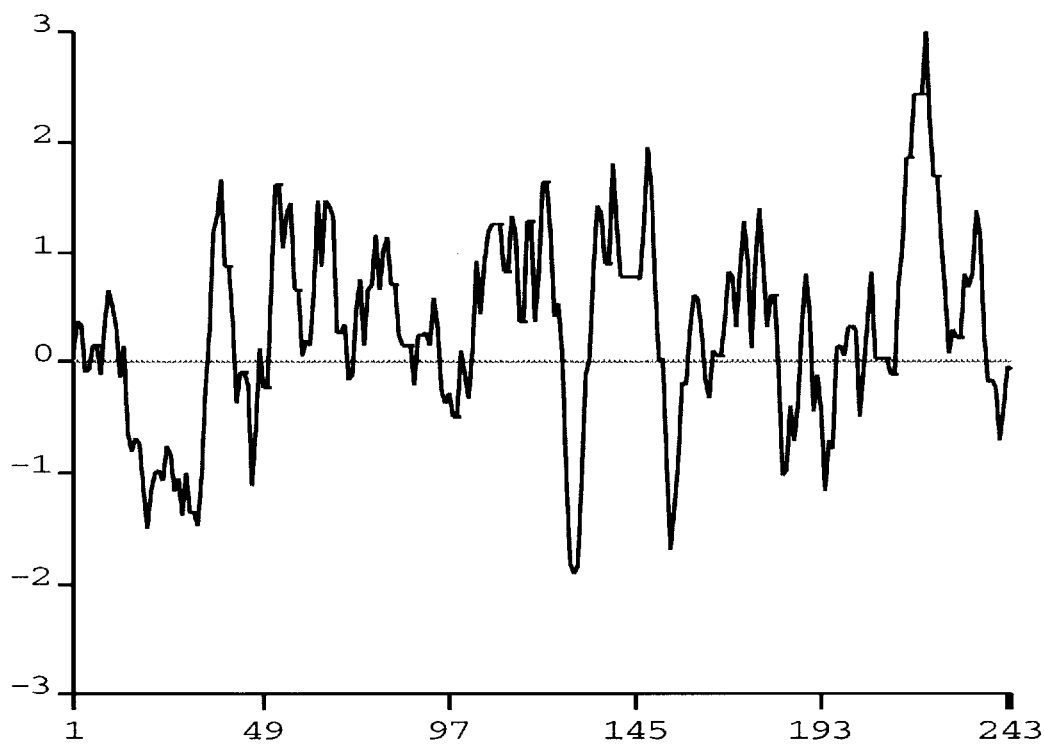
Figure 4C:
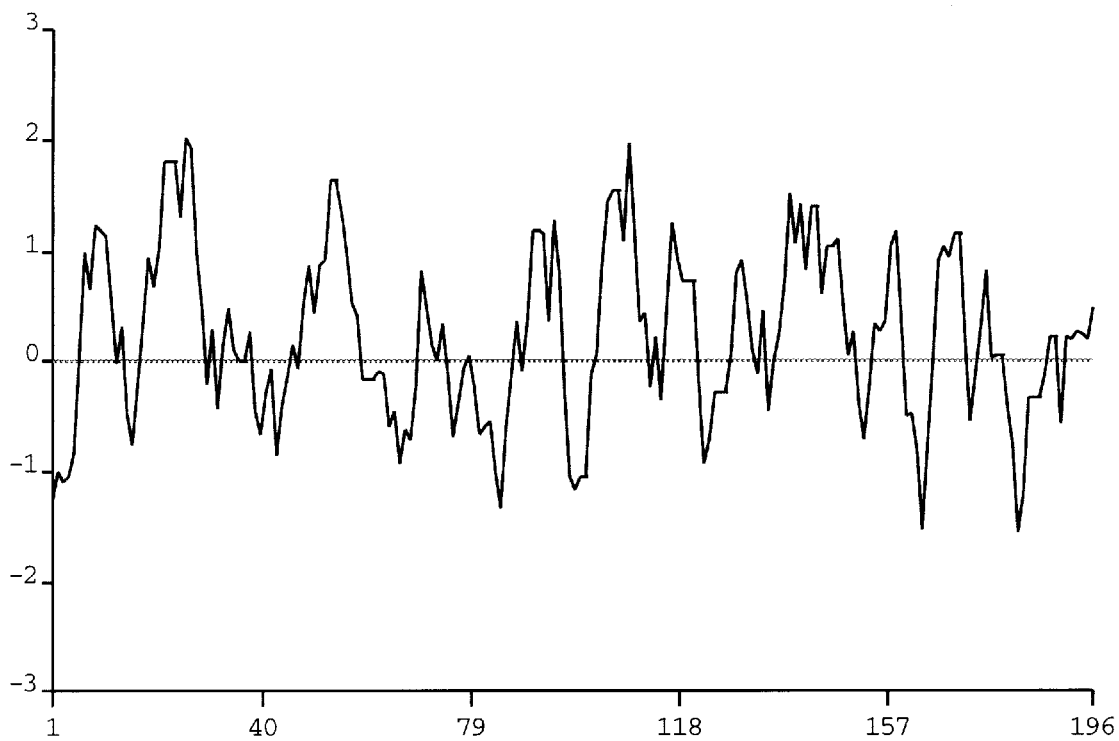
Figure 4D:
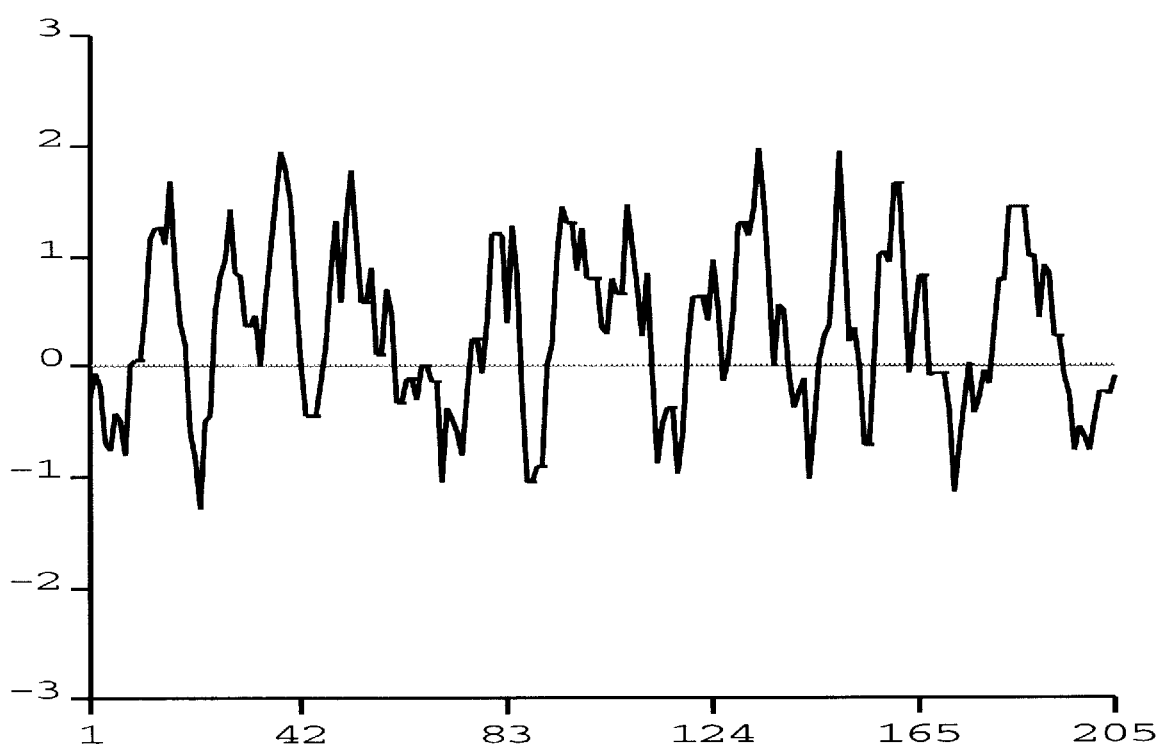

In one embodiment, the invention encompasses a polypeptide comprising the amino acid sequences of SEQ ID NO:1 and SEQ ID NO:2, as shown in FIGS. 1A, 1B, and 1C, and FIGS. 2A, 2B, 2C, and 2D, respectively. RGPS-1 and RGPS-2 are 159 and 243 amino acids in length, respectively. They both contain a potential G-protein coupled receptors signature, encompassing residues S57-I73 of RGPS-1 and S126-M142 of RGPS-2, as well as an RGS motif encompassing residues R30-L132 of RGPS-1 and K58-L177 of RGPS-2. In addition, RGPS-1 contains three potential N-glycosylation sites at N14-K17, N22-L25, and N156-F 159, four potential casein kinase II phosphorylation sites at T24-E27, S95-E98, S104-E107, and T119-E122, and five potential protein kinase C phosphorylation sites at S2-R4, S16-R18, T69-K71, S95-R97, and S104-R106. RGPS-2 contains one potential N-glycosylation site at N8-T11, one potential cAMP- and cGMP-dependent protein kinase phosphorylation site at K235-S238, three potential casein kinase II phosphorylation sites at T11-E14, S66-D69, and T220-E223, and three potential protein kinase C phosphorylation sites at S93-K95, T97-K99, and S161-K164. As shown in FIGS. 3A and 3B, RGPS-1 and RGPS-2 have chemical and structural homology with human BL34 (GI 299705; SEQ ID NO:5) and RGS4 (GI 1216373; SEQ ID NO:6). In particular, RGPS-1 shares 46% and 50% identity with human BL34 and RGS4, respectively; and RGPS-2 shares 46% and 37% identity with human BL34 and RGS4, respectively. As illustrated by FIGS. 4A–D, RGPS-1, RGPS-2, human BL34 and RGS4 have similar hydrophobicity plots. Northern analysis shows that RGPS-1 and RGPS-2 are expressed in various cDNA libraries: RGPS-1 has significant expression in inflamed tissues; and RGPS-2, in inflamed, immortalized or cancerous cells and tissues.

The invention also encompasses RGPS variants. A preferred RGPS variant is one having at least 80%, and more preferably 90%, amino acid sequence identity to the RGPS amino acid sequence (SEQ ID NO:1 or SEQ ID NO:3). A most preferred RGPS variant is one having at least 95% amino acid sequence identity to SEQ ID NO:1 or SEQ ID NO:3.

The invention also encompasses polynucleotides which encode RGPS. Accordingly, any nucleic acid sequence which encodes the amino acid sequence of RGPS can be used to generate recombinant molecules which express RGPS. In a particular embodiment, the invention encompasses the polynucleotide comprising the nucleic acid of SEQ ID NO:2 or SEQ ID NO:4 as shown in FIGS. 1A, 1B, and 1C, and FIGS. 2A, 2B, 2C, and 2D.

It will be appreciated by those skilled in the art that as a result of the degeneracy of the genetic code, a multitude of nucleotide sequences encoding RGPS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring RGPS, and all such variations are to be considered as being specifically disclosed.

Although nucleotide sequences which encode RGPS and its variants are preferably capable of hybridizing to the nucleotide sequence of the naturally occurring RGPS under appropriately selected conditions of stringency, it may be advantageous to produce nucleotide sequences encoding RGPS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding RGPS and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode RGPS and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding RGPS or any portion thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–11), and may be used at a defined stringency.

Altered nucleic acid sequences encoding RGPS which are encompassed by the invention include deletions, insertions, or substitutions of different nucleotides resulting in a polynucleotide that encodes the same or a functionally equivalent RGPS. The encoded protein may also contain deletions, insertions, or substitutions of amino acid residues which produce a silent change and result in a functionally equivalent RGPS. Deliberate amino acid substitutions may be made on the basis of similarity in polarity, charge, solubility, hydrophobicity, hydrophilicity, and/or the amphipathic nature of the residues as long as the biological activity of RGPS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding RGPS. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the MICCROLAB 2200 (Hamilton, Reno, Nev.), Peltier thermal cycler (PTC200; MJ Research, Watertown, Mass.) and the ABI 377 DNA sequencers (Perkin Elmer).

The nucleic acid sequences encoding RGPS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode RGPS, or fusion proteins or functional equivalents thereof, may be used in recombinant DNA molecules to direct expression of RGPS in appropriate host cells. Due to the inherent degeneracy of the genetic code, other DNA sequences which encode substantially the same or a functionally equivalent amino acid sequence may be produced and these sequences may be used to clone and express RGPS.

As will be understood by those of skill in the art, it may be advantageous to produce RGPS-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter sequences encoding RGPS for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

In another embodiment of the invention, natural, modified, or recombinant polynucleotides encoding RGPS may be ligated to a heterologous sequence to encode a fusion protein. For example, to screen peptide libraries for inhibitors of RGPS activity, it may be useful to encode a chimeric RGPS protein that can be recognized by a commercially available antibody. A fusion protein may also be engineered to contain a cleavage site located between a sequence encoding RGPS and the heterologous protein sequence, so that RGPS may be cleaved and purified away from the heterologous moiety.

In another embodiment, sequences encoding RGPS may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of RGPS, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of RGPS, or any part thereof, may be altered during direct synthesis and/or combined using chemical methods with sequences from other proteins, or any part thereof, to produce a variant polypeptide.

In order to express a biologically active RGPS, the nucleotide sequences encoding RGPS or functional equivalents, may be inserted into appropriate expression vectors, i.e., a vector which contains the necessary elements for the transcription and translation of the inserted coding sequence.

Methods which are well known to those skilled in the art may be used to construct expression vectors containing sequences encoding RGPS and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding RGPS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORTI plasmid (Gibco BRL), and the like, may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding RGPS, vectors based on SV40 or EBV may be used with an appropriate selectable marker.

In bacterial systems, a number of expression vectors may be selected depending upon the use intended for RGPS. For example, when large quantities of RGPS are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding RGPS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding RGPS may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express RGPS. For example, in one such system, *Autographa californica* nuclear polyhedrosis virus (AcNPV) is used as a vector to express foreign genes in *Spodoptera frugiperda* cells or in Trichoplusia larvae. The sequences encoding RGPS may be cloned into a non-essential region of the virus, such as the polyhedrin gene, and placed under control of the polyhedrin promoter. Successful insertion of RGPS will render the polyhedrin gene inactive and produce recombinant virus lacking coat protein. The recombinant viruses may then be used to infect, for example, *S. frugiperda* cells or Trichoplusia larvae in which RGPS may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding RGPS may be ligated into an adenovirus transcription/translation complex consisting of the late promoter and tripartite leader sequence. Insertion in a non-essential E1 or E3 region of the viral genome may be used to obtain a viable virus which is capable of expressing RGPS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding RGPS. Such signals include the ATG initiation codon and adjacent sequences. In cases where sequences encoding RGPS, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express RGPS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding RGPS is inserted within a marker gene sequence, recombinant cells containing sequences encoding RGPS can be identified by the absence of marker gene function. Alternatively, a marker gene can be placed in tandem with a sequence encoding RGPS under the control of a single promoter. Expression of the marker gene in response to induction or selection usually indicates expression of the tandem gene as well.

Alternatively, host cells which contain sequences encoding and expressing RGPS may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of the nucleic acid or protein.

The presence of polynucleotide sequences encoding RGPS can be detected by DNA—DNA or DNA-RNA hybridization or amplification using probes or portions or fragments of polynucleotides encoding RGPS. Nucleic acid amplification based assays involve the use of oligonucleotides or oligomers based on the sequences encoding RGPS to detect transformants containing DNA or RNA encoding RGPS. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of RGPS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on RGPS is preferred, but a competitive binding assay may be employed. These and other assays are described, among other places, in Hampton, R. et al. (1990; *Serological Methods*, a *Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding RGPS include oligolabeling, nick translation, end-labeling or PCR amplification using a labeled nucleotide. Alternatively, sequences encoding RGPS, or any portion thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding RGPS may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode RGPS may be designed to contain signal sequences which direct secretion of RGPS through a prokaryotic or eukaryotic cell membrane. Other recombinant constructions may be used to join sequences encoding RGPS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and RGPS may be used to facilitate purification. One such expression vector provides for expression of a fusion protein containing RGPS and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying RGPS from the fusion protein. A discussion of vectors which contain fusion proteins is provided in Kroll, D. J. et al. (1993; DNA Cell Biol. 12:441–453).

In addition to recombinant production, fragments of RGPS may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of RGPS may be chemically synthesized separately and combined using chemical methods to produce the full length molecule.

THERAPEUTICS

RGPS-1 and RGPS-2 share chemical and structural homology with the human BL34 (GI 299705) and the human RGS4 (GI 1216373). Northern analysis shows that the expression of RGPS is associated with cell proliferation and inflammation.

Increased expression of RGPS appears to be associated with decreased cell proliferation. Therefore, in one embodiment, RGPS or a fragment or derivative thereof may be administered to a subject to prevent or treat a disorder associated with cell proliferation. Disorders of cell proliferation include various types of cancer including, but not limited to, adenocarcinoma, leukemia, lymphoma, melanoma, and sarcoma, and particularly cancers of the bladder, bone, brain, breast, gastrointestinal tract, heart, kidney, liver, lung, ovary, pancreas, paraganglia, parathyroid, prostate, skin, testis, thyroid, tongue, and uterus.

In another embodiment, an agonist of RGPS or a derivative or fragment thereof may be used to modulate the activity of RGPS and to prevent or treat a disorder associated with cell proliferation including, but not limited to, those listed above.

In still another embodiment, a vector capable of expressing RGPS, or a fragment or a derivative thereof, may be used to prevent or treat a disorder associated with cell proliferation including, but not limited to, those listed above.

In another embodiment, RGPS or a fragment or derivative thereof may be administered to a subject to prevent or treat inflammation associated with any disorder including, but are not limited to, AIDS, Addison's disease, allergies, asthma, bronchitis, Crohn's disease, dermatomyositis, diabetes mellitus, emphysema, Graves' disease, irritable bowel syndrome, lupus erythematosus, myasthenia gravis, multiple sclerosis, urethritis, rheumatoid and osteoarthritis, thyroiditis, and ulcerative colitis.

In another embodiment, an agonist of RGPS or a fragment or derivative thereof may be used to modulate the activity of RGPS and to prevent or treat inflammation associated with any disorder including, but not limited to, those listed above.

In still another embodiment, a vector capable of expressing RGPS, or a fragment or a derivative thereof, may be used to prevent or treat inflammtion associated with any disorder including, but not limited to, those listed above.

Decreased expression of RGPS appears to be associated with increased cell proliferation. Therefore, in another embodiment, an antagonist or an inhibitor of RGPS, or a fragment or a derivative thereof, may be added to cells to stimulate cell proliferation. In particular, an antagonist of RGPS may be added to a cell or cells in vivo using delivery mechanisms such as liposomes, viral based vectors, or electroinjection for the purpose of promoting regeneration or differentiation of the cell or cells. In addition, an antagonist RGPS may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect such as sickle cell anemia or β thalassemia. In one aspect, an antibody specific for RGPS may be used directly as an antagonist, or indirectly as a targeting or delivery mechanism for bringing a pharmaceutical agent to cells or tissue which express RGPS.

In a still further embodiment, a vector expressing the complementary sequence or antisense of the polynucleotide encoding RGPS, or a fragment or a derivative thereof, may be used to stimulate cell proliferation, as detailed above.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of RGPS may be produced using methods which are generally known in the art. In particular, purified RGPS may be used to produce antibodies or to screen libraries of pharmaceutical agents to identify those which specifically bind RGPS.

The antibodies specific for RGPS may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with RGPS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to RGPS have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of RGPS amino acids may be fused with those of another protein such as keyhole limpet hemocyanin and antibody produced against the chimeric molecule.

Monoclonal antibodies to RGPS may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J Immunol. Methods 81:31–42; Cote, R. J. et al. (1983) Proc. Natl. Acad. Sci. 80:2026–2030; Cole, S. P. et al. (1985) Mol Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–55; Neuberger, M. S. et al. (1984) Nature 312:604–8; Takeda, S. et al. (1985) Nature 314:452–4). Alternatively, techniques described for the production of single chain antibodies may be adapted, using methods known in the art, to produce RGPS-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–37; Winter, G. et al. (1991) Nature 349:293–9).

Antibody fragments which contain specific binding sites for RGPS may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–81).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between RGPS and its specific antibody. A two-site, monoclonal-based immunoassay utilizing monoclonal antibodies reactive to two non-interfering RGPS epitopes is preferred, but a competitive binding assay may also be employed (Maddox, supra).

In another embodiment of the invention, the polynucleotides encoding RGPS, or any fragment thereof, or antisense molecules, may be used for therapeutic purposes. In one aspect, antisense to the polynucleotide encoding RGPS may be used in situations in which it would be desirable to block the transcription of mRNA. In particular, cells may be transformed with sequences complementary to polynucleotides encoding RGPS. Thus, antisense sequences may be used to modulate RGPS activity, or to achieve regulation of gene function. Such technology is now well known in the art, and sense or antisense oligomers or larger fragments, can be designed from various locations along the coding or control regions of sequences encoding RGPS.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding RGPS. These techniques are described both in Sambrook et al. (supra) and in Ausubel et al. (supra).

Genes encoding native RGPS can be turned off by transforming a cell or tissue with expression vectors which express high levels of the polynucleotide, or fragment thereof, which encodes RGPS. Such constructs may be used to introduce untranslatable sense or antisense sequences into a cell. Even in the absence of integration into the genomic DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding RGPS, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding RGPS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding RGPS. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of RGPS, antibodies to RGPS, mimetics, agonists, antagonists, or inhibitors of RGPS. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of RGPS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example RGPS or fragments thereof, antibodies of RGPS, agonists, antagonists or inhibitors of RGPS, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind RGPS may be used for the diagnosis of conditions or diseases characterized by expression of RGPS, or in assays to monitor patients being treated with RGPS, agonists, antagonists or inhibitors. The antibodies useful for diagnostic purposes may be prepared in the same manner as those described above for therapeutics. Diagnostic assays for RGPS include methods which utilize the antibody and a label to detect RGPS in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring RGPS are known in the art and provide a basis for diagnosing altered or abnormal levels of RGPS expression. Normal or standard values for RGPS expression are established by combining body fluids or cell extracts taken from normal mammalian subjects, preferably human, with antibody to RGPS under conditions suitable for complex formation. The amount of standard complex formation may be quantified by various methods, but preferably by photometric, means. Quantities of RGPS expressed in subject samples from biopsied tissues are compared with the standard values. Deviation between standard and subject values establishes the parameters for diagnosing disease.

In another embodiment of the invention, the polynucleotides encoding RGPS may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of RGPS may be correlated with disease. The diagnostic assay may be used to distinguish between absence, presence, and excess expression of RGPS, and to monitor regulation of RGPS levels during therapeutic intervention.

In one aspect, hybridization with PCR probes which are capable of detecting polynucleotide sequences, including genomic sequences, encoding RGPS or closely related molecules, may be used to identify nucleic acid sequences which encode RGPS. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding RGPS, alleles, or related sequences.

Probes may also be used for the detection of related sequences, and should preferably contain at least 50% of the nucleotides from any of the sequences encoding RGPS. The hybridization probes of the subject invention may be DNA or RNA and derived from the nucleotide sequences of SEQ ID NO:2 or SEQ ID NO:4 or from genomic sequence including promoter, enhancer elements, and introns of the naturally occurring RGPS.

Means for producing specific hybridization probes for DNAs encoding RGPS include the cloning of nucleic acid sequences encoding RGPS or RGPS derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding RGPS may be used for the diagnosis of conditions or disorders which are associated with the expression of RGPS. Examples of such conditions or disorders include various types of cancer such as adenocarcinoma, leukemia, lymphoma, melanoma, and sarcoma, and particularly cancers of the bladder, bone, brain, breast, gastrointestinal tract, heart, kidney, liver, lung, ovary, pancreas, paraganglia, parathyroid, prostate, skin, testis, thyroid, tongue, and uterus; and inflammation including, but not limited to, AIDS, Addison's disease, allergies, asthma, bronchitis, Crohn's disease, dermatomyositis, diabetes mellitus, emphysema, Graves' disease, irritable bowel syndrome, lupus erythematosus, myasthenia gravis, multiple sclerosis, urethritis, rheumatoid and osteoarthritis, thyroiditis, and ulcerative colitis. The polynucleotide sequences encoding RGPS may be used in Southern or northern analysis, dot blot, or other membrane-based technologies; in PCR technologies; or in dip stick, pin, ELISA or chip assays utilizing fluids or tissues from patient biopsies to detect altered RGPS expression. Such qualitative or quantitative methods are well known in the art.

In a particular aspect, the nucleotide sequences encoding RGPS may be useful in assays that detect activation or induction of various cancers, particularly those mentioned above. The nucleotide sequences encoding RGPS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding RGPS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of RGPS, a normal or standard profile for expression is established. This may be accomplished by combining body fluids or cell extracts taken from normal subjects, either animal or human, with a sequence, or a fragment thereof, which encodes RGPS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding RGPS may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of RGPS include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequence which encodes RGPS may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma, R. S. et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding RGPS on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, RGPS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between RGPS and the agent being tested, may be measured.

Another technique for drug screening which may be used provides for high throughput screening of compounds having suitable binding affinity to the protein of interest as described in published PCT application WO84/03564. In this method, as applied to RGPS large numbers of different small test compounds are synthesized on a solid substrate, such as plastic pins or some other surface. The test compounds are reacted with RGPS, or fragments thereof, and washed. Bound RGPS is then detected by methods well known in the art. Purified RGPS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding RGPS specifically compete with a test compound for binding RGPS. In this manner, the antibodies can be used to detect the presence of any peptide which shares one or more antigenic determinants with RGPS.

In additional embodiments, the nucleotide sequences which encode RGPS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

ADENINB01

A human adenoid cell cDNA library was made from a mixed cell population obtained from a surgical specimen resulting from a child's tonsillectomy. Such tonsils and adenoids comprise mixed lymphoid tissue which is in an active inflamed state with induced T and B cells, macrophages and plasma cells. Stratagene purified the mRNA from the lymphoid tissue and synthesized the cDNAs. Synthetic adaptor oligonucleotides were ligated onto cDNA ends enabling their insertion into Uni-ZAP vector system (Stratagene). Alternative unidirectional vectors include but are not limited to pcDNAI (Invitrogen, San Diego, Calif.) and pSHlox-1 (Novagen, Madison, Wis.).

The adenoid cDNA library can be screened with either DNA probes or antibody probes and the pBluescript phagemid (Stratagene) can be rapidly excised in vivo. The custom-constructed library phage particles-were infected into E. coli host strain XL1-BLUE (Stratagene).

THYMNOT02

The thymus library was constructed from the thymus tissue of a three year old Caucasian male (lot #93-122) obtained from the Keystone Skin Bank, International Institute for the Advancement of Medicine (Exton, Pa.). The frozen tissue was ground in a mortar and pestle and lysed immediately in a buffer containing guanidinium isothiocyanate. The lysate was extracted twice with phenol chloroform at pH 8.0 and centrifuged over a CsCl cushion using an SW28 rotor in an L8-70M ultracentrifuge (Beckman Instruments). The RNA was precipitated using 0.3M sodium acetate and 2.5 volumes of ethanol, resuspended in water and DNase treated for 15 min at 37° C. The RNA was isolated with the OLIGOTEX kit (QIAGEN Inc, Chatsworth, Calif.) and used to construct the cDNA library.

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on SEPHACRYL S400 to obtain sequences which exceeded 1000 bp in size. The size selected cDNAs were inserted into the LAMBDAZAP vector system (Stratagene); and the vector, which contains the PBLUESCRIPT phagemid (Stratagene), was transformed into cells of E. coli, strain XL1-BLUEMRF (Stratagene).

II Isolation and Sequencing of cDNA Clones

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

Phagemid DNA was purified using the QIAWELL-8 plasmid, QIAWELL PLUS, or QIAWELL ULTRA DNA purifications systems (QIAGEN Inc., Chatsworth, Calif.). This product line provides convenient, rapid and reliable high-throughput methods to lyse bacterial cells and isolate highly purified phagemid DNA. The DNA was eluted from the purification resin already prepared for DNA sequencing and other analytical manipulations.

Alternatively, plasmid DNA was purified using the Miniprep kit (Catalogue #77468, Advanced Genetic Technologies Corporation, Gaithersburg, Md.), a 96-well block kit with reagents for 960 purifications. The recommended protocol included with the kit was employed except for the following changes. Each of the 96 wells was filled with only 1 ml of sterile Terrific Broth (Catalog #22711, Gibco/BRL, Gaithersburg, Md.) with carbenicillin at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from MJ Research, Watertown, Mass.) and Applied Biosystems 377 DNA sequencing systems.

III Homology Searching of cDNA Clones and Their Deduced Proteins

After the reading frame was determined, the nucleotide sequences of the Sequence Listing or amino acid sequences deduced from them were used as query sequences against databases such as GenBank, SwissProt, BLOCKS, and Pima II. These databases which contain previously identified and annotated sequences, were searched for regions of homology (similarity) using BLAST, which stands for Basic Local Alignment Search Tool (Altschul (1993) supra, Altschul (1990) supra).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach, as detailed in Karlin et al. (supra) and incorporated herein by reference, searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum } BLAST \text{ score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding RGPS occurs. Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding RGPS

Incyte clone 158909 or 343504, or SEQ ID NOs:2 or 4 is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK kit (Qiagen Inc.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 μl of liquid LB/2x Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3x) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots or the blots are exposed in a Phosphoimager cassette (Molecular Dynamics, Sunnyvale, Calif.), hybridization patterns are compared visually.

VII Complementary Polynucleotides, Antisense Molecules

Complementary polynucleotides or antisense molecules comprising the sequence encoding RGPS, or any part thereof, are used to inhibit in vivo or in vitro expression of naturally occurring RGPS. Although use of antisense oligonucleotides, comprising about 20 base-pairs, is specifically described, essentially the same procedure is used with larger cDNA fragments. An oligonucleotide based on the sequences encoding RGPS is used to inhibit expression of naturally occurring RGPS. The complementary oligonucleotide is designed from the most unique 5' sequence as shown in and used either to inhibit transcription by preventing promoter binding to the upstream nontranslated sequence or translation of a transcript encoding RGPS by preventing the ribosome from binding. Using an appropriate portion of the signal and 5' sequence of SEQ ID NO:2 or SEQ ID NO:4, an effective antisense oligonucleotide includes any 15–20 nucleotides spanning the region which translates into the signal or 5' coding sequence of the polypeptide as shown in FIGS. 1A, 1B, and 1C, and FIGS. 2A, 2B, 2C, and 2D.

VIII Expression of RGPS

Expression of RGPS is accomplished by subcloning the cDNAs into appropriate vectors and transforming the vectors into host cells. In this case, the cloning vector, pSport, previously used for the generation of the cDNA library is used to express RGPS in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of RGPS into the bacterial growth media which can be used directly in the following assay for activity.

IX Demonstration of RGPS Activity

Cell lines or tissues transformed with a vector containing SEQ ID NO:1 or SEQ ID NO:3 can be assayed for RGPS activity by immunoblotting. Cells are denatured in SDS in the presence of β-mercaptoethanol, nucleic acids removed by ethanol precipitation, and proteins purified by acetone precipitation. Pellets are resuspended in 20 mM tris buffer at pH 7.5 and incubated with Protein G-SEPHAROSE precoated with an antibody specific for RGPS. After washing, the SEPHAROSE beads are boiled in electrophoresis sample buffer, and the eluted proteins subjected to SDS-PAGE. The SDS-PAGE is transferred to a nitrocellulose membrane for immunoblotting, and the RGPS activity is assessed by visualizing and quantifying bands on the blot using the antibody specific for RGPS as the primary antibody and $^{125}$I-labeled IgG specific for the primary antibody as the secondary antibody.

X Production of RGPS Specific Antibodies

RGPS that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring RGPS Using Specific Antibodies

Naturally occurring or recombinant RGPS is substantially purified by immunoaffinity chromatography using antibodies specific for RGPS. An immunoaffinity column is constructed by covalently coupling RGPS antibody to an activated chromatographic resin, such as CnBr-activated SEPHAROSE (Pharmacia & Upjohn). After the coupling, the resin is blocked and washed according to the manufacturer's instructions.

Media containing RGPS is passed over the immunoaffinity column, and the column is washed under conditions that allow the preferential absorbance of RGPS (e.g., high ionic strength buffers in the presence of detergent). The column is eluted under conditions that disrupt antibody/RGPS binding (e.g., a buffer of pH 2–3 or a high concentration of a chaotrope, such as urea or thiocyanate ion), and RGPS is collected.

XII Identification of Molecules Which Interact with RGPS

RGPS or biologically active fragments thereof are labeled with $^{125}$I Bolton-Hunter reagent (Bolton, A. E. and W. M. Hunter (1973) Biochem. J. 133: 529–39). Candidate molecules previously arrayed in the wells of a multi-well plate are incubated with the labeled RGPS, washed and any wells with labeled RGPS complex are assayed. Data obtained using different concentrations of RGPS are used to calculate values for the number, affinity, and association of RGPS with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO:1.

2. A hybridization probe comprising the polynucleotide of claim 1 and a detectable label.

3. An isolated and purified polynucleotide which is complementary to the polynucleotide sequence of claim 1.

4. A hybridization probe comprising the polynucleotide of claim 6 and a detectable label.

5. An expression vector comprising the polynucleotide of claim 1.

6. A host cell transfected or transformed with the expression vector of claim 5.

7. A method for producing a polypeptide comprising the amino acid sequence of SEQ ID NO:1, the method comprising the steps of:
   a) culturing the host cell of claim 6 under conditions suitable for the expression of the polypeptide; and
   b) recovering the polypeptide from the host cell culture.

8. An isolated and purified polynucleotide comprising SEQ ID NO:2.

* * * * *

UNITED STATES PATENT AND TRADEMARK OFFICE
CERTIFICATE OF CORRECTION

| | |
|---|---|
| PATENT NO. | : 5,882,890 |
| DATED | : March 16, 1999 |
| INVENTOR(S) | : Hillman et al. |

Page 1 of 1

It is certified that error appears in the above-identified patent and that said Letters Patent is hereby corrected as shown below:

<u>Column 41,</u>
Line 24, delete "claim 6" and insert -- claim 3 --.

Signed and Sealed this

Thirty-first Day of July, 2001

Attest:

*Nicholas P. Godici*

Attesting Officer

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 159 amino acids
( B ) TYPE: amino acid
( C ) STRANDEDNESS: single
( D ) TOPOLOGY: linear ( v i i ) IMMEDIATE SOURCE:
( A ) LIBRARY: ADENINB01
( B ) CLONE: 158909

( x i ) SEQUENCE DESCRIPTION: SEQ ID NO:1:

```
Met  Ser  Arg  Arg  Asn  Cys  Trp  Ile  Cys  Lys  Met  Cys  Arg  Asn  Lys  Ser
 1              5                        10                       15

Lys  Arg  Pro  Pro  Ser  Asn  Leu  Thr  Leu  Glu  Glu  Val  Leu  Arg  Trp  Ala
              20                       25                       30

Gln  Ser  Phe  Glu  Asn  Leu  Met  Ala  Thr  Lys  Tyr  Gly  Pro  Ile  Ile  Tyr
              35                       40                       45

Ala  Ala  Tyr  Leu  Lys  Thr  Glu  His  Ser  Asp  Gln  Asn  Ile  Gln  Phe  Trp
         50                       55                       60

Met  Ala  Cys  Glu  Thr  Tyr  Lys  Lys  Ile  Ala  Ser  Arg  Trp  Ser  Arg  Ile
65                       70                       75                       80

Ser  Arg  Ala  Lys  Lys  Leu  Tyr  Lys  Ile  Tyr  Ile  Gln  Pro  Gln  Ser  Pro
                   85                       90                       95

Arg  Glu  Ile  Asn  Ile  Asp  Ser  Ser  Thr  Arg  Glu  Thr  Ile  Ile  Arg  Asn
              100                      105                      110

Ile  Gln  Glu  Pro  Thr  Glu  Thr  Cys  Phe  Glu  Glu  Ala  Gln  Lys  Ile  Val
              115                      120                      125

Tyr  Met  His  Met  Glu  Arg  Asp  Ser  Tyr  Pro  Arg  Phe  Leu  Lys  Ser  Glu
         130                      135                      140

Met  Tyr  Gln  Lys  Leu  Leu  Lys  Thr  Met  Gln  Ser  Asn  Asn  Ser  Phe
145                      150                      155
```

( 2 ) INFORMATION FOR SEQ ID NO:2:

( i ) SEQUENCE CHARACTERISTICS:
( A ) LENGTH: 981 base pairs
( B ) TYPE: nucleic acid
( C ) STRANDEDNESS: single
( D ) TOPOLOGY: linear ( v i i ) IMMEDIATE SOURCE:
( A ) LIBRARY: ADENINB01
( B ) CLONE: 158909

( x i ) SEQUENCE DESCRIPTION: SEQ ID NO:2:

```
CGCCTATAAT  GAGACAGTAA  AATTCTTTTA  CTCTGGGAAA  AATAAAATGC  TGGGTGTCTC     60

ACAAAATTTC  AGAACCTGAT  TTCAAACGGA  TCATAACAAA  GAGGAGATCA  AATTTAGCAT    120

GGTGGACTGC  TCGACAGGAT  ACATTTGTCA  ATGGAATGTT  TCCACATATT  ATACCACCAA    180

CATGAGAAAA  AAATGATCAT  TGTTTATTTG  AAGCTTGAAA  AATGAGCAGG  CGGAATTGTT    240
```

-continued

```
GGATTTGTAA AATGTGCAGA AATAAATCTA AGAGGCCCCC TTCAAACCTT ACCTTGGAGG      300
AAGTATTACG GTGGGCCCAG TCTTTTGAAA ATTTAATGGC TACAAAATAT GGTCCAATTA      360
TCTATGCCGC ATATTTAAAA ACGGAACACA GTGACCAAAA TATTCAATTC TGGATGGCAT      420
GTGAAACCTA TAAGAAAATT GCCTCACGGT GGAGCAGAAT TCTAGGGCA AAGAAGCTTT       480
ATAAGATTTA CATCCAGCCA CAGTCCCCTA GAGAGATTAA CATTGACAGT TCGACAAGAG      540
AGACTATCAT CAGGAACATT CAGGAACCCA CTGAAACATG TTTTGAAGAA GCTCAGAAAA      600
TAGTCTATAT GCATATGGAA AGGGATTCCT ACCCCAGATT TCTAAAGTCA GAAATGTACC      660
AAAAACTTTT GAAAACTATG CAGTCCAACA ACAGTTTCTG ACTACAACTC AAAAGTTTAA      720
ATAGAAAACA GTATATTGAA AGTGGTGGGT TTGATCTTTT TATTTAGAAA CCCACAAAAT      780
CAGAAACACA GTACAAATAA AACAGAAATC AAACTATAAG TTGACTTTTA GTTCCTAAAA      840
AGAAACATAT TTCAAAAGCA ATGGAATCTA GAATTCTTAT AACATGAATA ACAAAATGTA      900
CAGCAAGCCT ATGTAGTTCA ATTAATATAT AAGGACAAGG AAGGTCTTCT TCATGATACA      960
AGCATTATAA AGTTTTTACT G                                                981
```

( 2 ) INFORMATION FOR SEQ ID NO:3:

( i ) SEQUENCE CHARACTERISTICS:
        ( A ) LENGTH: 243 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: THYMNOT02
        ( B ) CLONE: 343504

( x i ) SEQUENCE DESCRIPTION: SEQ ID NO:3:

```
Met Ser Ser Gln Ile Arg Gln Asn Tyr Ser Thr Asp Val Glu Ala Ala
 1           5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Val Ala Leu Glu Gly Val
            35              40                  45

Ser His Phe Phe Arg Glu Leu Ala Glu Glu Ala Gln Gly Leu Arg
    50                  55                  60

Ala Ser Pro Glu Asp Ala Lys Pro Ala Trp Arg Pro Pro Ser Asp Ile
65                  70              75                      80

His Asp Ser Asp Gly Ser Ser Ser Ser His Gln Ser Leu Lys Ser
                85                  90                  95

Thr Ala Lys Trp Ala Ala Ser Leu Glu Asn Leu Leu Glu Asp Pro Glu
            100                 105                 110

Gly Val Lys Arg Phe Arg Glu Phe Leu Lys Lys Glu Phe Ser Glu Glu
            115                 120                 125

Asn Val Leu Phe Trp Leu Ala Cys Glu Asp Phe Lys Lys Met Gln Asp
            130                 135                 140

Lys Thr Gln Met Gln Glu Lys Ala Lys Glu Ile Tyr Met Thr Phe Leu
145                 150                 155                 160

Ser Ser Lys Ala Ser Ser Gln Val Asn Val Glu Gly Gln Ser Arg Leu
                165                 170                 175

Asn Glu Lys Ile Leu Glu Glu Pro His Pro Leu Met Phe Gln Lys Leu
            180                 185                 190

Gln Asp Gln Ile Phe Asn Leu Met Lys Tyr Asp Ser Tyr Ser Arg Phe
            195                 200                 205
```

| Leu | Lys | Ser | Asp | Leu | Phe | Leu | Lys | His | Lys | Arg | Thr | Glu | Glu | Glu | Glu |
| | | 210 | | | | 215 | | | | 220 | | | | | |

| Glu | Asp | Leu | Pro | Asp | Ala | Gln | Thr | Ala | Ala | Lys | Arg | Ala | Ser | Arg | Ile |
| 225 | | | | 230 | | | | | 235 | | | | | 240 | |

Tyr Asn Thr ( 2 ) INFORMATION FOR SEQ ID NO:4:

( i ) SEQUENCE CHARACTERISTICS:
        ( A ) LENGTH: 1225 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: THYMNOT02
        ( B ) CLONE: 343504

( x i ) SEQUENCE DESCRIPTION: SEQ ID NO:4:

```
CGGACGGTGG  GACGGTTCCC  GCGGGTCTGT  CTCTTGCTTC  GACAGTGTTT  GGACGGAACA    60
GATCCGGGGA  CTCTCTTCCA  GCCTCCGACC  GCCCTCCGAT  TTCCTCTCCG  CTTGCAACCT   120
CCGGGACCAT  CTTCTCGGCC  ATCTCCTGCT  TCTGGGACCT  GCCAGCACCG  TTTTTGTGGT   180
TAGCTCCTTC  TTGCCAACCA  ACCATGAGCT  CCCAGATTCG  TCAGAATTAT  TCCACCGACG   240
TGGAGGCAGC  CGTCAACAGC  CTGGTCAATT  TGTACCTGCA  GGCCTCCTAC  ACCTACCTCT   300
CTCTGGGCTT  CTATTTCGAC  CGCGATGATG  TGGCTCTGGA  AGGCGTGAGC  CACTTCTTCC   360
GCGAACTGGC  CGAGGAAGAA  GCGCAAGGGC  TACGAGCGTC  TCCTGAAGAT  GCAAAACCAG   420
CGTGGCGGCC  GCCGTCAGAC  ATCCACGACA  GCGATGGCAG  TTCCAGCAGC  AGCCACCAGA   480
GCCTCAAGAG  CACAGCCAAA  TGGGCGGCAT  CCCTGGAGAA  TCTGCTGGAA  GACCCAGAAG   540
GCGTGAAAAG  ATTTAGGGAA  TTTTTAAAAA  AGGAATTCAG  TGAAGAAAAT  GTTTTGTTTT   600
GGCTAGCATG  TGAAGATTTT  AAGAAAATGC  AAGATAAGAC  GCAGATGCAG  GAAAAGGCAA   660
AGGAGATCTA  CATGACCTTT  CTGTCCAGCA  AGGCCTCATC  ACAGGTCAAC  GTGGAGGGGC   720
AGTCTCGGCT  CAACGAGAAG  ATCCTGGAAG  AACCGCACCC  TCTGATGTTC  CAGAAACTCC   780
AGGACCAGAT  CTTTAATCTC  ATGAAGTACG  ACAGCTACAG  CCGCTTCTTA  AAGTCTGACT   840
TGTTTTTAAA  ACACAAGCGA  ACCGAGGAAG  AGGAAGAAGA  TTTGCCTGAT  GCTCAAACTG   900
CAGCTAAAAG  AGCTTCCAGA  ATTTATAACA  CATGAGCCCC  AAAAAGCCG   GGACTGGCAG   960
CTTTAAGAAG  CAAAGGAATT  TCCTCTCAGG  ACCGTGCCGG  GTTTATCATT  GCTTTGTTAT  1020
TTGTAAGGAC  TGAAATGTAC  AAAACCCTTC  AATGGGATGT  GTGTTTATT  AACTGCTTCA  1080
CCAGTAAATT  TTGCATGATG  GCTAAGCTAA  CATAMMAAAA  GAMTAATAAT  AACTTGGAAG  1140
TTTTAGTTTA  CAAAACAGAG  ATTCCTTCAA  CACTGGNCAC  GTCGAGCATT  TTTNGTAGCT  1200
TNAATTAAAC  CTCATGTAAT  GCCCA                                           1225
```

( 2 ) INFORMATION FOR SEQ ID NO:5:

( i ) SEQUENCE CHARACTERISTICS:
        ( A ) LENGTH: 196 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 299705

( x i ) SEQUENCE DESCRIPTION: SEQ ID NO:5:

| Met | Pro | Gly | Met | Phe | Phe | Ser | Ala | Asn | Pro | Lys | Glu | Leu | Lys | Gly | Thr |
| 1 | | | | 5 | | | | | 10 | | | | | 15 | |

| Thr | His | Ser | Leu | Leu | Asp | Asp | Lys | Met | Gln | Lys | Arg | Arg | Pro | Lys | Thr |
| | | | 20 | | | | | 25 | | | | | 30 | | |

| Phe | Gly | Met | Asp | Met | Lys | Ala | Tyr | Leu | Arg | Ser | Met | Ile | Pro | His | Leu |
| | | 35 | | | | | 40 | | | | | 45 | | | |

| Glu | Ser | Gly | Met | Lys | Ser | Ser | Lys | Ser | Lys | Asp | Val | Leu | Ser | Ala | Ala |
| | 50 | | | | | 55 | | | | | 60 | | | | |

| Glu | Val | Met | Gln | Trp | Ser | Gln | Ser | Leu | Glu | Lys | Leu | Leu | Ala | Asn | Gln |
| 65 | | | | | 70 | | | | | 75 | | | | | 80 |

| Thr | Gly | Gln | Asn | Val | Phe | Gly | Ser | Phe | Leu | Lys | Ser | Glu | Phe | Ser | Glu |
| | | | | 85 | | | | | 90 | | | | | 95 | |

| Glu | Asn | Ile | Glu | Phe | Trp | Leu | Ala | Cys | Glu | Asp | Tyr | Lys | Lys | Thr | Glu |
| | | | 100 | | | | | 105 | | | | | 110 | | |

| Ser | Asp | Leu | Leu | Pro | Cys | Lys | Ala | Glu | Glu | Ile | Tyr | Lys | Ala | Phe | Val |
| | | | 115 | | | | | 120 | | | | | 125 | | |

| His | Ser | Asp | Ala | Ala | Lys | Gln | Ile | Asn | Ile | Asp | Phe | Arg | Thr | Arg | Glu |
| | | 130 | | | | | 135 | | | | | 140 | | | |

| Ser | Thr | Ala | Lys | Lys | Ile | Lys | Ala | Pro | Thr | Pro | Thr | Cys | Phe | Asp | Glu |
| 145 | | | | | 150 | | | | | 155 | | | | | 160 |

| Ala | Gln | Lys | Val | Ile | Tyr | Thr | Leu | Met | Glu | Lys | Asp | Ser | Tyr | Pro | Arg |
| | | | | 165 | | | | | 170 | | | | | 175 | |

| Phe | Leu | Lys | Ser | Asp | Ile | Tyr | Leu | Asn | Leu | Leu | Asn | Asp | Leu | Gln | Ala |
| | | | 180 | | | | | 185 | | | | | 190 | | |

| Asn | Ser | Leu | Lys |
| | | 195 | |

( 2 ) INFORMATION FOR SEQ ID NO:6:

( i ) SEQUENCE CHARACTERISTICS:
        ( A ) LENGTH: 205 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1216373

( x i ) SEQUENCE DESCRIPTION: SEQ ID NO:6:

| Met | Cys | Lys | Gly | Leu | Ala | Gly | Leu | Pro | Ala | Ser | Cys | Leu | Arg | Ser | Ala |
| 1 | | | | 5 | | | | | 10 | | | | | 15 | |

| Lys | Asp | Met | Lys | His | Arg | Leu | Gly | Phe | Leu | Leu | Gln | Lys | Ser | Asp | Ser |
| | | | 20 | | | | | 25 | | | | | 30 | | |

| Cys | Glu | His | Asn | Ser | Ser | His | Asn | Lys | Lys | Asp | Lys | Val | Val | Ile | Cys |
| | | | 35 | | | | | 40 | | | | | 45 | | |

| Gln | Arg | Val | Ser | Gln | Glu | Glu | Val | Lys | Lys | Trp | Ala | Glu | Ser | Leu | Glu |
| | | 50 | | | | | 55 | | | | | 60 | | | |

| Asn | Leu | Ile | Ser | His | Glu | Cys | Gly | Leu | Ala | Ala | Phe | Lys | Ala | Phe | Leu |
| 65 | | | | | 70 | | | | | 75 | | | | | 80 |

| Lys | Ser | Glu | Tyr | Ser | Glu | Glu | Asn | Ile | Asp | Phe | Trp | Ile | Ser | Cys | Glu |
| | | | | 85 | | | | | 90 | | | | | 95 | |

| Glu | Tyr | Lys | Lys | Ile | Lys | Ser | Pro | Ser | Lys | Leu | Ser | Pro | Lys | Ala | Lys |
| | | | | 100 | | | | | 105 | | | | | 110 | |

| Lys | Ile | Tyr | Asn | Glu | Phe | Ile | Ser | Val | Gln | Ala | Thr | Lys | Glu | Val | Asn |
| | | | 115 | | | | | 120 | | | | | 125 | | |

| Leu | Asp | Ser | Cys | Thr | Arg | Glu | Glu | Thr | Ser | Arg | Asn | Met | Leu | Glu | Pro |
| | | 130 | | | | | 135 | | | | | 140 | | | |

-continued

| Thr 145 | Ile | Thr | Cys | Phe | Asp 150 | Glu | Ala | Gln | Lys | Lys 155 | Ile | Phe | Asn | Leu | Met 160 |
| Glu | Lys | Asp | Ser | Tyr 165 | Arg | Arg | Phe | Leu | Lys 170 | Ser | Arg | Phe | Tyr | Leu 175 | Asp |
| Leu | Val | Asn | Pro 180 | Ser | Ser | Cys | Gly | Ala 185 | Glu | Lys | Gln | Lys | Gly 190 | Ala | Lys |
| Ser | Ser | Ala 195 | Asp | Cys | Ala | Ser | Leu 200 | Val | Pro | Gln | Cys | Ala 205 | | | |